United States Patent [19]

Carr

[11] 4,264,579

[45] Apr. 28, 1981

[54] DENTIFRICES

[75] Inventor: John F. Carr, Knutsford, England

[73] Assignee: Colgate-Palmolive Company, New York, N.Y.

[21] Appl. No.: 104,492

[22] Filed: Dec. 17, 1979

Related U.S. Application Data

[63] Continuation-in-part of Ser. No. 28,295, Apr. 9, 1979, abandoned.

[30] Foreign Application Priority Data

May 30, 1978 [GB] United Kingdom ............... 24226/78

[51] Int. Cl.³ .......................... A61K 7/16; A61K 7/18
[52] U.S. Cl. ...................................... 424/57; 424/49; 424/52
[58] Field of Search ....................... 424/49-58

[56] References Cited

U.S. PATENT DOCUMENTS

| | | | |
|---|---|---|---|
| 3,840,657 | 10/1974 | Norfleet | 424/49 |
| 3,929,987 | 12/1975 | Colodney et al. | 424/52 |
| 3,935,304 | 1/1976 | Januszewski et al. | 424/49 |
| 3,935,305 | 1/1976 | Delaney et al. | 424/49 |
| 3,944,661 | 3/1976 | Colodney et al. | 424/49 |
| 3,946,108 | 3/1976 | Tomlinson et al. | 424/49 |
| 4,020,154 | 4/1977 | Perla et al. | 424/49 |
| 4,060,599 | 11/1977 | Cordon | 424/49 |
| 4,069,311 | 1/1978 | Mannara | 424/49 |
| 4,130,636 | 12/1978 | Tomlinson | 424/52 |
| 4,144,322 | 3/1979 | Cordon et al. | 424/49 |

FOREIGN PATENT DOCUMENTS 1476063 6/1977 United Kingdom ..................... 424/49

*Primary Examiner*—Shep K. Rose
*Attorney, Agent, or Firm*—Robert L. Stone; Murray M. Grill; Herbert S. Sylvester

[57] ABSTRACT

An opaque extrudable toothpaste containing as the abrasive and/or polishing agent a major proportion of sodium aluminosilicate and a minor proportion of another abrasive which is wholly or predominantly a soft abrasive such as dicalcium phosphate, in a vehicle which is wholly or predominantly water.

2 Claims, No Drawings

DENTIFRICES

This is a continuation-in-part of application Ser. No. 28,295, filed Apr. 9, 1979, now abandoned.

This invention relates to toothpastes, particularly toothpastes of reduced density.

The abrasive or abrasive/polishing systems of known toothpaste compositions contribute significantly to the cost of the toothpaste, either directly in view of their intrinsic value, or indirectly in view of their effect on the other required toothpaste constituents. Since they comprise a substantial part of weight of a toothpaste, they also are responsible for much of its density. Many of the most commonly used abrasives for opaque toothpastes are becoming more difficult and expensive to obtain in suitable grades and it is therefore desirable to minimize the quantities used. Furthermore toothpastes using these materials as the sole or major abrasive require further expensive constituents such as thickeners in order to produce an effective and acceptable product. A glycerine or sorbitol vehicle is often used for this purpose and any reduction here too with increase in the amount of water while retaining satisfactory rheology is desirable.

Sodium aluminosilicate (SAS) is also known as a toothpaste constituent, both as a polishing agent generally for visually clear toothpastes in grades which have refractive indices close to that of commonly employed toothpaste humectants, such as glycerine and sorbitol (e.g., about 1.44–1.47) which grades are not molecular sieves, as well as in its molecular sieve form.

The abbreviation "SAS" is used throughout this specification to refer to sodium aluminosilicate. The abbreviation "DCP" is used throughout this specification to refer to dicalcium phosphate in its dihydrated form. All parts and percentages given throughout this specification are by weight unless otherwise indicated.

It is an object of the present invention to produce a toothpaste having an improved abrasive system.

According to the present invention an opaque extrudable toothpaste comprises about 50 to 90% by weight of a liquid vehicle at least about 60% of which is water and the remainder being humectant and about 10 to 50% by weight of an abrasive agent containing sodium aluminosilicate in major amount and a minor proportion of another soft water-insoluble dental abrasive selected from the group consisting of dicalcium phosphate, insoluble sodium metaphosphate and alumina trihydrate.

It has been found that SAS can be used in partial replacement for more conventional abrasives such as DCP, insoluble metaphosphate (IMP) and alumina trihydrate (AT) at a lower level, e.g. 1 part of SAS can replace more than about 2 parts of DCP, IMP and AT and still give desirable rheology and abrasivity. Thus the DCP, IMP or AT content of a toothpaste can be reduced by using SAS, and in addition a comparable performance can be obtained with a toothpaste of reduced density. As toothpastes can be sold by volume rather than by weight this can offer significant cost savings. Furthermore the use of SAS results in a toothpaste of increased viscosity compared say to conventional DCP/CaCO$_3$ toothpastes thus allowing the use of water in at least partial replacement of the sorbitol or glycerine previously referred to.

A slightly increased proportion of gelling agent may be necessary in view of the lower sorbitol of glycerine content in order to maintain consistency and to avoid separation of the toothpaste components.

In British Pat. No. 1,476,063 a dentifrice containing a major amount of SAS and a minor amount of calcium carbonate is described. The toothpaste of the present invention is advantageous over the dentifrice of this patent in that substantially more of the soft water insoluble dental abrasives DCP, IMP and AT can be replaced by 1 part of SAS than is replaced by calcium carbonate. For example, SAS (Alusil ET) replaces about 2.4 times its weight of DCP, about 2.3 times its weight of IMP and about 2.6 times its weight of AT and only about 2.0 and 2.1 times its weight of calcium carbonate.

The SAS used in the invention may be any of those available in the United Kingdom under the following names:

ALUSIL N—(Crosfields) ALUSIL AS–(Crosfields)
ALUSIL ET—(Crosfields)
SIDENT P (previously "DEGUSSA" P 820-Degussa), or may be any comparable SAS material suitable for use as for instance the precipitated silica Zeo 49 of Huber in which a small amount of combined alumina is present in a suitable form of SAS. Mixtures of these materials may be used.
Polishing agents grades of SAS are described in U.S. Pat. No. 3,906,090 and 3,911,102.

The SAS may be used in an amount from 5% to 20% by weight of the toothpaste, the total abrasive content being from 10% to 55% by weight of the toothpaste. The SAS may form at least about 50% by weight of the total abrasive content.

The DCP which may be the soft water-insoluble dental abrasive present with the SAS may be such as is available in the United Kingdom under the name VICTOR DCP (Stauffer) or may be any comparable DCP material suitable for use as a dental abrasive. Mixtures of such grades may be used.

The DCP may be present in the toothpaste in an amount in the range of 5% to 30%, preferably 10% to 25%, but in lower amount than the SAS.

Other soft water-insoluble abrasive materials which may form part or all of the said other abrasives are:
IMP;
AT (e.g., ALCOA C333 of Alcoa).

These materials may be present in the dentifrice in amounts in the range of 5% to 30%. Mixtures may be used.

The polishing ability of the dentifrice may also be supplemented with a small amount, e.g., up to 15%, of a hard, water-insoluble dental abrasive such as calcined alumina or zirconium silicate.

The dentifrice liquid vehicle may comprise about 60% up to 100% water. The non-aqueous component, when present, may be any conventional dentifrice liquid vehicle constituent such as sorbitol, glycerine, propylent glycol, polyethylene glycol or mixtures thereof. The liquid vehicle is formulated to produce, with the other constituents, a creamy mass extrudable from a collapsible tube, e.g., an aluminium tube. The humectant properties of the sorbitol or glycerine may be useful.

The dentifrice typically also includes a gelling agent such as a natural and synthetic gum or gum-like materials, e.g., Irish moss, gum tragacanth, methyl cellulose, hydroxyethyl cellulose, sodium carboxymethyl cellulose, polyvinyl pyrrolidone, or starch. The gelling agent may be present in an amount up to 10% preferably about 0.2 to 5%, most preferably about 1.2 to 2%, of the toothpaste.

Organic surface-active agents may be included in the toothpastes of the invention to increase prophylactic action and assist in schieving thorough and complete dispersion of the composition throughout the oral cavity. The organic surface-active agents may be anionic, nonionic, ampholytic or cationic in nature, and it is preferred to employ as the surface-active agent a detersive material which imparts to the toothpaste detersive and foaming properties. Suitable such detergents are water-soluble salts of higher fatty acid monoglyceride monssulphates such as sodium lauryl sulphate, alkyl aryl sulphonates such as sodium docecyl benzene sulphonate, higher alkyl sulphoacetates, higher fatty acid esters of 1,2 dihydroxy propane sulphonates, and substantially saturated higher aliphatic acyl amides of lower aliphatic amino carboxylic acid compounds, such as those having 12 to 16 carbons in the higher fatty acid, alkyl or acyl radicals. Examples of the last mentioned amides are N-lauroyl sarcosine, and the sodium potassium and ethanolamine salts of N-lauroyl, N-myristoyl or N-palmitoyl sarcosine which should be substantially free from soap or similar higher fatty acid material which tends to reduce substantially the effect of these compounds. The use of these sarcosinate compounds in toothpastes of the present invention is particularly advantageous since these materials exhibit a prolonged and marked effect in the inhibition of acid formation in the oral cavity due to carbohydrates breakdown in addition to exerting some reduction in the solubility of tooth enamel in acid solutions.

Other particularly suitable surface-active materials include nonionic agents such as condensates or sorbitan monostearate with approximately 60 moles of ethylene oxide, condensates of ethylene oxide with propylene oxide condensates of propylene glycol (available under the trademark PLURONIC), and amphoteric agents such as quaternized imidazole derivatives which are available under the trademark MIRANOL such as "Miranol $C_2M$". Cationic surface-active germicides and antibacterial compounds such as diisobutylphenoxyethoxyethyl dimethyl benzyl ammonium chloride, benzyl dimethyl stearyl ammonium chloride, tertiary amines having one fatty alkyl group (of from 12 to 18 carbon atoms) and two (poly) oxyethylene groups attached to the nitrogen (typically containing a total of from 2 to 50 ethanoxy groups per molecule) and salts thereof with acids, and compounds of the structure

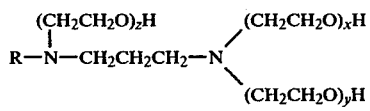

where R is a fatty alkyl group containing from 12 to 18 carbon atoms, and x, y, and z total 3 or higher, as well as salts thereof with mineral or organic acids, may also be used. It is preferred to use from 0.05% to 5% by weight of surface-active material in the toothpaste.

Various other materials may be incorporated in the toothpaste. Examples are coloring or whitening agents, preservatives, silicones, chlorophyll compounds, and ammoniated materials such as urea and diammoniumphosphate, and mixtures thereof. These adjuvants are incorporated in the toothpaste in amounts which do not substantially adversely affect the properties and characteristics desired.

The toothpaste typically has a pH (determined directly on the toothpaste) in the range from 4.5 to 11.5.

If desired, the pH may be adjusted with an acidic material such as benzoic acid or citric acid, or an alkaline material such as sodium hydroxide to achieve a particular value. Buffering agents, e.g., phosphate buffers, may be used.

A fluoride-providing compound may also be present. These compounds may be slightly soluble in water or may be fully water soluble. They are characterised by their ability to release fluoride ions in water and by substantial freedom from reaction with other compounds of the oral preparation. Among these materials are inorganic fluoride salts, such as suitable alkali metal, alkaline earth metal, and heavy metal salts, for example, sodium fluoride, potassium fluoride, ammonium fluoride, a copper fluoride such as cuprous fluoride, zinc fluoride, a tin fluoride such as stannous fluoride, or stannous chlorofluoride, barium fluoride, sodium fluorosilicate, ammonium fluorosilicate, sodium fluorozirconate, sodium monofluorophosphate, aluminium mono- and difluorophosphate, and fluorinated sodium calcium pyrophosphate. Alkali metal and tin fluorides, such as sodium and stannous fluorides and also sodium monofluorophosphate are preferred.

The fluoride providing compound may be present in an effective but non-toxic amount providing from 0.01% to 1% by weight of fluorine.

The dentifrice toothpaste formulations of the following Examples illustrate the invention. All amounts are by weight unless otherwise indicated.

EXAMPLE

| | 1 % | 1A % | 2 % | 2A % | 3 % | 3A % |
|---|---|---|---|---|---|---|
| Sorbitol | — | — | 16.0 | 16.0 | — | — |
| Glycerine | 19.8 | 19.8 | 9.9 | 9.9 | 19.8 | 19.8 |
| Sodium Carboxymethyl Cellulose (CMC) | 1.5 | 1.5 | 1.5 | 1.5 | 1.5 | 1.5 |
| Sodium Saccharin | 0.2 | 0.2 | 0.2 | 0.2 | 0.2 | 0.2 |
| Water | 49.4 | 22.4 | 44.34 | 24.34 | 49.4 | 26.4 |
| TiO$_2$ | 1.0 | 1.0 | — | — | 1.0 | 1.0 |
| Sodium Monofluorophosphate (MFP) | 0.8 | 0.8 | 0.76 | 0.76 | 0.8 | 0.8 |
| Alusil ET | 15.0 | — | 15.0 | — | 15.0 | — |
| Alcoa C 333 | 10.0 | 52.0 | — | — | — | — |
| IMP | — | — | 10.0 | 45.0 | — | — |
| VICTOR DCP | — | — | — | — | 10.0 | 48.0 |
| Sodium Lauryl Sulphate (SLS) | 1.5 | 1.5 | 1.5 | 1.5 | 1.5 | 1.5 |
| Flavor | 0.8 | 0.8 | 0.8 | 0.8 | 0.8 | 0.8 |
| pH | 11.1 | 9.0 | 10.8 | 5.7 | 10.4 | 7.2 |
| Density | 1.26 | 1.58 | 1.27 | 1.54 | 1.26 | 1.51 |
| Enemal Abrasivity | 59.4 | 84.9 | 63.3 | 115.2 | 32.4 | 43.6 |
| Dentine Abrasivity | 48.7 | 121.0 | 52.9 | 101.2 | 47.2 | 75.5 |

The formulations all produced opaque toothpastes of an extrudable consistency.

The abrasivities of toothpaste grades SAS and DCP are as follows:

| | To Dentine | To Enamel |
|---|---|---|
| SAS | 20 to 25 | 45 to 50 |
| DCP | 35 to 50 | 35 to 50 |

It is thus seen that the dentifrices of the invention offer advantages of density and in abrasivity. Some tendency towards synergism in abrasivity of a mixture of SAS and DCP is also shown.

What is claimed is:

1. An opaque extrudable toothpaste comprised of about 50 to 90% by weight of a liquid vehicle at least about 60% of which is water and the remainder being humectant and about 10 to 50% by weight of an abrasive agent comprising about 5 to 20% by weight of the toothpaste of sodium aluminosilicate and about 5 to 30% by weight of the toothpaste of another soft water-insoluble dental abrasive selected from the group consisting of dicalcium phosphate, insoluble sodium metaphosphate and alumina trihydrate, the amount of said dicalcium phosphate when present being lower than the amount of said sodium aluminosilicate.

2. The toothpaste as claimed in claim 1 wherein said abrasive agent comprises about 15% by weight of the toothpaste of sodium aluminosilicate and about 10% by weight of the toothpaste of dicalcium phosphate.

* * * * *